US012502484B2

(12) United States Patent
Matsumoto

(10) Patent No.: US 12,502,484 B2
(45) Date of Patent: Dec. 23, 2025

(54) SYRINGE BARREL GRIP, BARREL ASSEMBLY, AND SYRINGE

(71) Applicant: TERUMO KABUSHIKI KAISHA, Tokyo (JP)

(72) Inventor: Fumiya Matsumoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 763 days.

(21) Appl. No.: 17/871,334

(22) Filed: Jul. 22, 2022

(65) Prior Publication Data

US 2022/0355038 A1 Nov. 10, 2022

Related U.S. Application Data

(63) Continuation of application No. PCT/JP2021/003898, filed on Feb. 3, 2021.

(30) Foreign Application Priority Data

Mar. 24, 2020 (JP) ................................ 2020-052233

(51) Int. Cl.
*A61M 5/31* (2006.01)

(52) U.S. Cl.
CPC ................................ *A61M 5/3137* (2013.01)

(58) Field of Classification Search
CPC .................... A61M 5/3137; A61M 2005/3139
See application file for complete search history.

(56) References Cited

U.S. PATENT DOCUMENTS

| | | | |
|---|---|---|---|
| 2014/0012227 A1 | 1/2014 | Sigg et al. |
| 2015/0105734 A1 | 4/2015 | Bryant et al. |
| 2016/0081849 A1 | 3/2016 | Tsai et al. |
| 2017/0290987 A1 | 10/2017 | Mandaroux et al. |

FOREIGN PATENT DOCUMENTS

| | | |
|---|---|---|
| JP | 2014028114 A | 2/2014 |
| JP | 2015080688 A | 4/2015 |
| JP | 2015517860 A | 6/2015 |
| JP | 2017527406 A | 9/2017 |
| JP | 2019510589 A | 4/2019 |
| WO | 2017073658 A1 | 5/2017 |

OTHER PUBLICATIONS

International Search Report (PCT/ISA/210) with translation and Written Opinion (PCT/ISA/237) mailed on Mar. 30, 2021, by the Japan Patent Office as the International Searching Authority for International Application No. PCT/JP2021/003898.

English Translations of the International Search Report (Form PCT/ISA/210) and the Written Opinion of the International Searching Authority (Form PCT/ISA/237) issued Mar. 30, 2021, by the Japan Patent Office in corresponding International Application No. PCT/JP2021/003898. (5 pages).

*Primary Examiner* — Laura A Bouchelle
(74) *Attorney, Agent, or Firm* — BUCHANAN INGERSOLL & ROONEY PC

(57) ABSTRACT

A syringe barrel grip is attached to a syringe barrel including a flange in which a pair of flange straight portions is formed. A flange housing portion of the grip includes a flange rotation restricting portion that restricts relative rotation between the grip and the flange that has entered the flange rotation restricting portion by rotating the barrel by a predetermined angle in a state where the flange is housed in a flange insertion portion, and there is a gap for allowing a sterilization gas to flow between a lower inner peripheral surface of the grip and the barrel in a state where the flange is housed in the flange rotation restricting portion.

20 Claims, 10 Drawing Sheets

SYRINGE BARREL GRIP, BARREL ASSEMBLY, AND SYRINGE

CROSS-REFERENCES TO RELATED APPLICATIONS

This application is a continuation of International Patent Application No. PCT/JP2021/003898 filed on Feb. 3, 2021, which claims priority to Japanese Patent Application No. 2020-052233 filed on Mar. 24, 2020, the entire content of both of which is incorporated herein by reference.

TECHNOLOGICAL FIELD

The present invention generally relates to a syringe barrel grip attached to a syringe barrel, and a barrel assembly and a syringe each including the syringe barrel grip.

BACKGROUND DISCUSSION

Some drug-filled syringes (prefilled syringes) use a plunger that is not coupled to a gasket in order to prevent medical errors. To such a prefilled syringe, a clip (backstop) for preventing a plunger from moving to a proximal end side and falling off from a barrel is attached. An example is disclosed in Japanese Patent Application Publication No. 2015-517860 (U.S. Patent Application Publication No. 2015/0105734 and U.S. Patent Application Publication No. 2019/0365565).

In addition, in order to facilitate gripping and operation of a syringe, it is also known to attach a clip (grip) including a finger hook portion protruding outward to a proximal end portion of a barrel (Patent Literature 2). An example is disclosed in International Patent Application Publication No. 2017/073658 (U.S. Patent Application Publication No. 2018/0243509).

These clips are each fitted to an outer peripheral surface of a barrel at a cylindrical fitting portion and firmly attached to a syringe so as not to rattle or come off during operation of the syringe.

SUMMARY

In recent years, in ophthalmic use and the like, higher sterility of not only a drug to be administered and a portion in contact with the drug but also the entire prefilled syringe including a grip is required. Therefore, the present inventors have studied an application of a surface sterilization method with a small heat load, such as hydrogen peroxide sterilization, EOG sterilization, or $NO_2$ sterilization, to a prefilled syringe to which a grip is attached. These surface sterilization methods perform sterilization with a gas (sterilization gas), and in order to achieve higher sterility, the sterilization gas preferably comes into contact with a wider area of a surface of the prefilled syringe.

The syringe barrel grip disclosed here has good operability and capable of achieving higher sterility in a state of being attached to a syringe barrel, and a barrel assembly and a syringe each including such a syringe barrel grip.

According to one aspect, a syringe barrel grip is configured to be attached to a syringe barrel, wherein the syringe barrel includes a cylindrical body and a flange disposed on the cylindrical body, with the flange protruding outward from the cylindrical body and including a pair of flange straight portions parallel to one another and spaced apart from one another by a first width. The syringe barrel grip comprises a flange housing portion configured to house the flange of the syringe barrel when the syringe barrel grip is attached to the syringe barrel. The flange housing portion includes: a side surface opening formed on a side surface of the syringe barrel grip through which the flange of the syringe barrel is configured to pass as the flange of the syringe is being housed in the flange housing portion; a flange insertion portion extending in an internal direction of the syringe barrel grip from the side surface opening and configured to receive the flange of the syringe barrel that has passed through the side surface opening; and a flange rotation restricting portion that communicates with the flange insertion portion, extends into the syringe barrel grip, receives the flange of the syringe barrel as a result of relative rotation between the flange of the syringe barrel and the syringe barrel grip when the flange of the syringe barrel is positioned in the flange insertion portion, and restricts relative rotation between the syringe barrel grip and the flange of the syringe barrel after the flange of the syringe barrel is positioned in the flange rotation restricting portion. The flange insertion portion includes a first pair of grip straight portions spaced apart from one another by a second width that is greater than the first width, and the flange rotation restricting portion includes a second pair of grip straight portions spaced apart from one another by a third width that is greater than the first width, with each of the second pair of grip straight portions being inclined with respect to a respective one of the first pair of grip straight portions. The flange rotation restricting portion is configured such that when the flange of the syringe barrel is positioned in the flange rotation restricting portion, front sides of the pair of flange straight portions are located between the second pair of grip straight portions, and rear sides of the pair of flange straight portions are located between the first pair of grip straight portions. The flange rotation restricting portion of the flange housing portion is configured such that when the flange of the syringe barrel is positioned in the flange rotation restricting portion, a lower inner peripheral surface of the syringe barrel grip is not in contact with the barrel so that a gap exists between the lower inner peripheral surface of the syringe barrel grip and the barrel, with the gap allowing a sterilization gas to flow between the lower inner peripheral surface of the grip and the barrel.

According to another aspect, a syringe comprises a barrel assembly comprised of a syringe barrel and a syringe barrel grip, with the syringe barrel including a cylindrical body and a flange disposed at a proximal end of the cylindrical body, and the flange protruding outward away from the cylindrical body and including a pair of flange straight portions that are parallel to one another and that face away from one another, with the flat straight portions being spaced apart from each other by a first width. The barrel assembly also comprises a gasket slidably housed in the cylindrical body of the syringe barrel, and a plunger positionable in the cylindrical body of the syringe barrel for slidably moving the gasket in the cylindrical body of the syringe barrel. The syringe barrel grip comprises a flange housing portion in which is positioned the flange of the syringe barrel, wherein the flange housing portion includes: a side surface opening formed on a side surface of the syringe barrel grip through which the flange of the syringe barrel passes as the flange of the syringe is introduced into the flange housing portion; a flange rotation restricting portion in which the flange is positioned and that restricts relative rotation between the syringe barrel grip and the flange; and a flange insertion portion between the side surface opening and the flange rotation restricting portion, the flange insertion portion being configured to receive the flange of the syringe barrel that has passed through the flange insertion portion and before the flange of the syringe barrel is moved to the flange rotation restricting portion of the flange housing portion. The flange insertion portion includes a first pair of grip straight portions spaced apart from one another by a second width that is greater than the first width, and the flange rotation restricting portion includes a second pair of grip straight portions spaced apart from one another by a third width that is greater than the first width, and each of the second pair of grip straight portions is inclined with respect to a respective one of the first pair of grip straight portions. The flange is positioned in the flange rotation restricting portion of the flange housing portion such that front sides of the pair of flange straight portions are located between the second pair of grip straight portions, and rear sides of the pair of flange straight portions are located between the first pair of grip straight portions. The flange is positioned in the flange rotation restricting portion of the flange housing portion such that a lower inner peripheral surface of the grip is not in contact with the barrel so that a gap exists between the lower inner peripheral surface of the grip and the barrel, the gap allowing a sterilization gas to flow between the lower inner peripheral surface of the grip and the barrel.

Another aspect involves method comprising: introducing a flange at one end of a cylindrical syringe barrel into a side surface opening located on a side surface of a flange housing portion of a syringe barrel grip, wherein the flange protrudes outwardly away from the cylindrical body and includes a pair of flange straight portions parallel to one another and spaced apart by a first distance. The flange housing portion also includes a flange insertion portion extending in an internal direction of the syringe barrel grip from the side surface opening, and a flange rotation restricting portion that communicates with the flange insertion portion. The flange insertion portion includes a first pair of grip straight portions spaced apart by a distance that is greater than the first distance, and the flange rotation restricting portion includes a second pair of grip straight portions spaced apart by a distance that is greater than the first distance. The method also involves moving the flange which has been introduced into the side surface opening into the flange insertion portion of the flange housing portion such that the pair of flange straight portions are located between the first pair of grip straight portions of the flange insertion portion, with each of the second pair of grip straight portions being inclined with respect to a respective one of the first pair of grip straight portions, and relatively rotating the cylindrical syringe barrel and the syringe barrel grip while the flange of the cylindrical syringe barrel is in the flange insertion portion to move the flange from the flange insertion portion of the flange housing portion of the syringe barrel grip to the flange rotation restricting portion of the flange housing portion of the syringe barrel grip. The flange of the cylindrical syringe barrel located in the flange rotation restricting portion of the flange housing portion of the syringe barrel grip is positioned so that front sides of the pair of flange straight portions are located between the second pair of grip straight portions, and rear sides of the pair of flange straight portions are located between the first pair of grip straight portions. In addition, the flange of the cylindrical syringe barrel located in the flange rotation restricting portion of the flange housing portion of the syringe barrel grip is configured so that a gap for allowing a sterilization gas to flow between a lower inner peripheral surface of the grip and the cylindrical syringe barrel.

DETAILED DESCRIPTION

Set forth below with reference to the accompanying drawings is a detailed description of embodiments of a syringe barrel grip, and a barrel assembly and syringe including such a syringe barrel grip, representing examples of the new syringe barrel grip, barrel assembly and syringe disclosed here.

Figure 1:
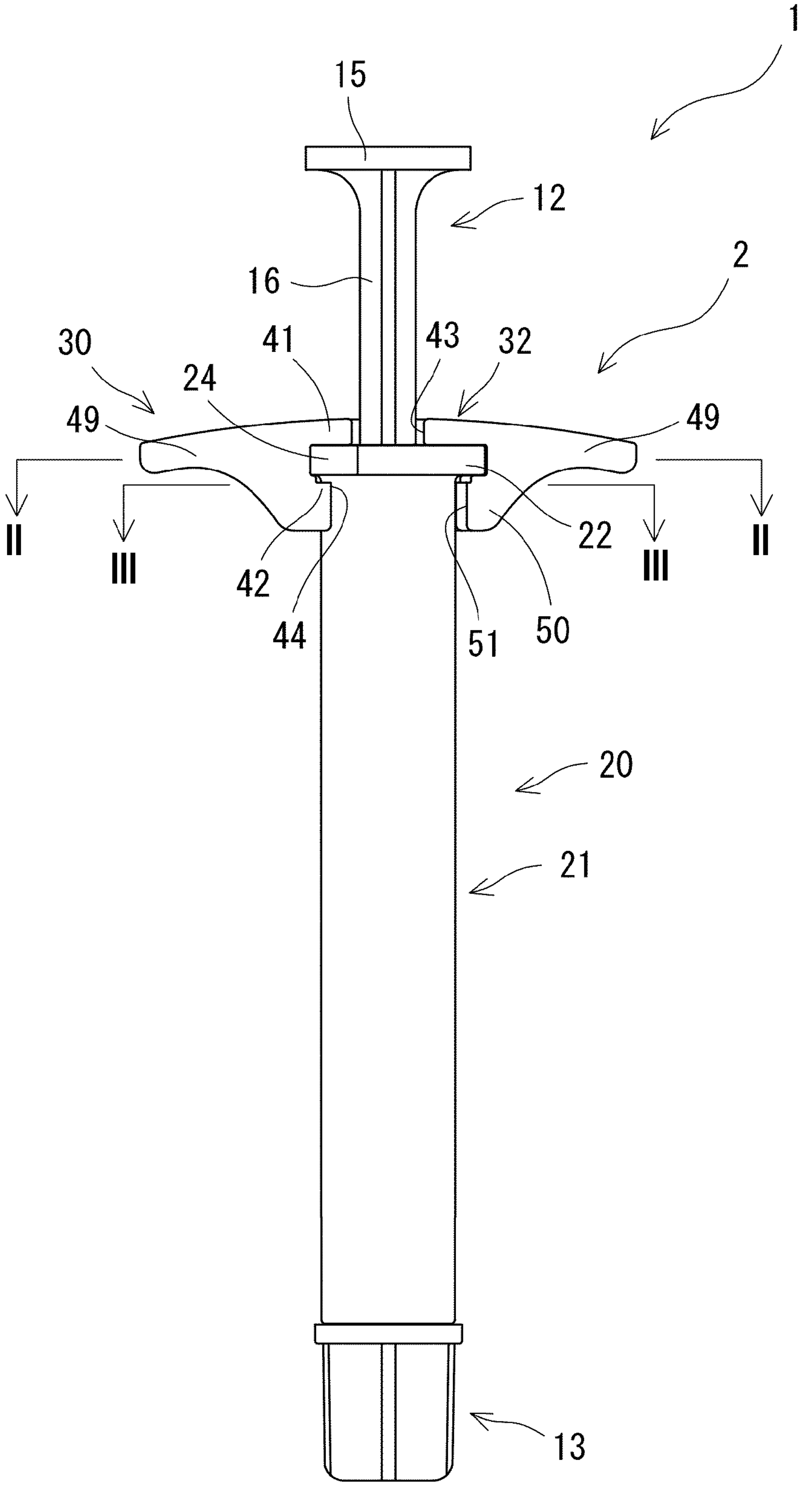
FIG. 1 is a front view illustrating an embodiment of a syringe disclosed as one example.

In the following description, an upper side in FIG. 1 (the side on which a flange 22 of a syringe barrel 20 is formed) is defined as a proximal end side or an upper side, a lower side in FIG. 1 (the side on which a nozzle portion 23 of the syringe barrel 20 is disposed) is defined as a distal end side or a lower side, and the vertical direction in FIG. 1 is referred to as an axial direction (the axial direction of the syringe barrel 20 or a cylindrical body 21).

As illustrated in FIGS. 1 to 6, a syringe 1 includes: a barrel assembly 2 including a syringe barrel 20 (hereinafter, also simply referred to as a barrel 20) and a syringe barrel grip 30 (hereinafter, also simply referred to as a grip 30) attached to the barrel 20; a gasket 11 slidably housed in the barrel 20; and a plunger 12 for moving the gasket 11.

The barrel 20 includes a cylindrical body 21 and a flange 22 (thickness t) disposed on the cylindrical body 21, protruding outward (in a direction orthogonal to the axial direction of the barrel 20). The flange 22 includes a pair of flange straight portions 24 and 24 (width w) facing away from each other in opposite directions in parallel (i.e., the flange straight portions or flat surfaces 24, 24 of the flange 22 are parallel to one another and face away from each other in opposite directions). In the present embodiment, the cylindrical body 21 of the barrel 20 has a circular (annular) outer shape and a circular (annular) inner shape in a cross section taken along a plane orthogonal to the axial direction of the cylinder body 21 as a whole. A distal end opening portion (nozzle portion) 23 for discharging a drug is disposed at a distal end portion of the barrel 20.

In addition, the barrel 20 includes a collar 25 covering a proximal end side portion of the nozzle portion 23. A barrel side screwing portion (female screwing portion) is formed on an inner surface of the collar 25.

The nozzle portion 23 is sealed by a seal cap 13 to prevent leakage of a drug 60 stored in the barrel 20 and to prevent the aseptically filled drug 60 from coming into contact with outside air.

Examples of a constituent material from which the barrel 20 may be fabricated include various resins such as a polyolefin including polyethylene and polypropylene, polystyrene, polyamide, polycarbonate, polyvinyl chloride, poly-(4-methylpentene-1), an acrylic resin, an acrylonitrile-butadiene-styrene copolymer, a polyester including polyethylene terephthalate, a cyclic polyolefin polymer, and a cyclic olefin copolymer. Among these resins, resins such as polypropylene, a cyclic polyolefin polymer, and a cyclic olefin copolymer are preferable because the resins are easily molded and have heat resistance. A cyclic olefin polymer or a cyclic olefin copolymer having high transparency such that a drug solution filled inside can be visually confirmed from the outside and having heat resistance capable of withstanding high-pressure steam sterilization is particularly preferable as a material for forming the barrel 20.

The seal cap 13 includes a body portion 18 having a proximal end side hollow portion that houses the nozzle portion 23 of the barrel 20, and a seal member 19 housed in the body portion 18 and disposed at a distal end portion of the proximal end side hollow portion. In addition, on an outer surface of the proximal end side hollow portion, a cap side screwing portion (male screwing portion) capable of being screwed with the barrel side screwing portion (female screwing portion) formed on an inner surface of the collar 25 is formed.

Examples of a material for forming the seal cap include various resins such as polypropylene, polyethylene, polystyrene, polyamide, polycarbonate, polyvinyl chloride, poly-(4-methylpentene-1), an acrylic resin, an acrylonitrile-butadiene-styrene copolymer, a polyester including polyethylene terephthalate, and a cyclic polyolefin. Among these resins, resins such as polypropylene and a cyclic polyolefin are preferable because the resins are easily molded and have heat resistance.

As a material for forming the seal member 19, an elastic material such as a natural rubber, a synthetic rubber including an isoprene rubber, a butyl rubber, a butadiene rubber, a fluororubber, and a silicone rubber, or a thermoplastic elastomer including an olefin-based elastomer and a styrene-based elastomer is preferable.

The gasket 11 housed in the barrel 20 is made of an elastic rubber or a synthetic resin. The gasket 11 includes a substantially cylindrical body portion extending with substantially the same outer diameter and a plurality of annular ribs disposed on an outer surface of the body portion. Outer surfaces of the annular ribs are in liquid-tight contact with an inner surface of the barrel 20 and are slidable in a liquid-tight state.

As a material for forming the gasket 11, it is preferable to use an elastic rubber (for example, a butyl rubber, a latex rubber, or a silicone rubber), a synthetic resin (for example, a styrene-based elastomer such as an SBS elastomer or an SEBS elastomer, or an olefin-based elastomer such as an ethylene-α olefin copolymer elastomer), or the like.

The plunger 12 is made of a hard or semi-hard resin. In this embodiment, the plunger 12 includes a small disk-shaped gasket pressing portion 14 disposed at a distal end thereof, a disk-shaped pressing operation portion 15 disposed at a proximal end thereof, and a shaft portion 16 having a cross-shaped cross section and extending in the axial direction of the barrel 20 between the gasket pressing portion 14 and the pressing operation portion 15. The shaft portion 16 may be a columnar shaft. The columnar shaft may have a rod shape, a circular columnar shape, a polygonal columnar shape, a circular cylindrical shape, a polygonal cylindrical shape, or the like.

In this embodiment, the plunger 12 is not connected to the gasket 11, and can abut on a proximal end portion of the gasket 11 at the gasket pressing portion 14. The gasket 11 can be moved to a distal end side (in the distal direction) by pressing after abutment.

A distal end side portion (the gasket pressing portion 14 and a part of a distal end side of the shaft portion 16) of the plunger 12 is housed in the barrel 20 (cylindrical body 21). The plunger 12 includes a stopper portion 17 (stopper) that is disposed in a portion (shaft portion 16) housed in the barrel 20, abuts on the grip 30 (stopper abutment portion 31) described in detail later, and restricts detachment (removal) of the plunger 12 from the barrel 20. More specifically, the stopper portion 17 has a disk shape having an outer shape (outer diameter) smaller than the inner shape (inner diameter) of the barrel 20 (cylindrical body 21) and larger than the outer shape (maximum diameter portion) of the shaft portion 16 of the plunger 12.

A constituent material from which the plunger 12 may be fabricated includes a hard or semi-hard resin such as high-density polyethylene, polypropylene, polystyrene, or polyethylene terephthalate.

In the syringe 1, the drug (drug solution) 60 is stored (filled) in the barrel 20 (in a space formed between the seal cap 13 and the gasket 11).

The drug 60 to be stored is not particularly limited, and examples thereof include a vitamin, a sugar, an electrolyte, an organic acid, a mineral, a fat emulsion, an amino acid, a protein, and an organ preparation mainly as nutrients. Examples thereof further include a drug for a central nervous system, such as a general anesthetic, an antipyretic analgesic, or a general cold preparation, a drug for a peripheral nervous system, such as a local anesthetic or a muscle relaxant, a drug for a sensory organ, such as an ophthalmic agent, a metabolic drug such as a circulatory drug, a respiratory drug, a digestive drug, an urogenital anal drug, a hormonal agent, an antibiotic, or a diabetes drug, a biological preparation such as an antitumor drug, an allergic drug, an antibacterial agent, or an antiviral agent, and a prescription drug such as distilled water or physiological saline mainly as therapeutic agents. Examples thereof further include a vaccine mainly as a preventive agent and a contrast agent mainly as a diagnostic agent.

Many of the exemplified drugs each contain, as a main component, a synthetic low molecular weight compound, a synthetic middle molecular weight compound, a biopharmaceutical such as a polypeptide preparation or a protein preparation, or a biologically derived pharmaceutical such as a blood preparation, but these substances can be used as drugs regardless of the applications described above. In addition, a substance corresponding to a molecular target drug such as an antibody can also be used as a drug. A dosage form of each of these drugs is preferably a liquid even in a drug having a solid dosage form such as a powder or a granule in addition to a liquid from a viewpoint of usability.

In addition, as the drug 60, an ophthalmic drug that can be administered by puncture can be used. Examples of a specific target disease for which such an ophthalmic drug is used include choroidal neovascularization, age-related macular degeneration (both exudative and atrophic), macular edema secondary to retinal vein occlusion (RVO) (including both branch retinal vein occlusion (bRVO) and central retinal vein occlusion (cRVO)), choroidal neovascularization secondary to pathologic myopia (PM), diabetic macular edema (DME), diabetic retinopathy, and proliferative retinopathy. Examples of the drug to be used include ranibizumab [trade name: LUCENTIS (registered trademark)], bevacizumab [trade name: AVASTIN (registered trademark)], and aflibercept [trade name: EYLEA (registered trademark)], which are anti-VEGF antibodies used as therapeutic agents for age-related macular degeneration, and conbercept known as VEGF-TrapEye (aflibercept intravitreal injection solution).

The structure of the syringe barrel grip 30 will be described with reference to the embodiment illustrated in FIGS. 1 to 14.

Figure 2:
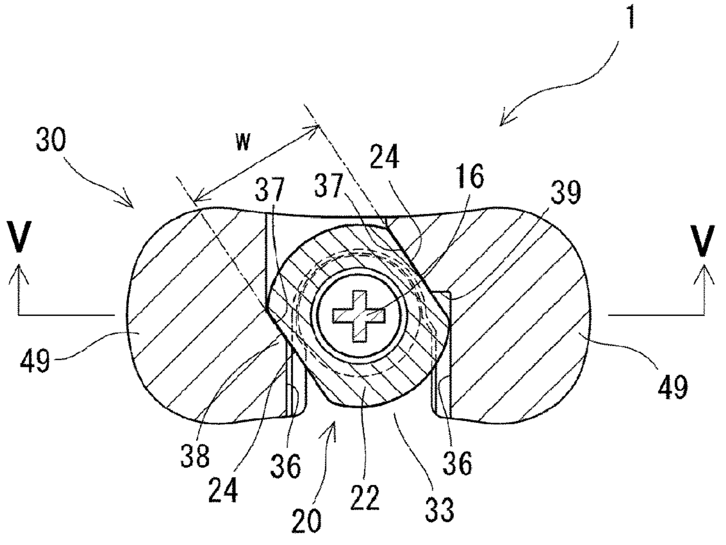
FIG. 2 is a cross-sectional view taken along line II-II in FIG. 1.

The syringe barrel grip 30 of this embodiment includes a flange housing portion 32 that houses or surrounds/encloses the flange 22. As illustrated in FIG. 2, the flange housing portion 32 includes: a side surface opening 33 formed on a side surface of the grip 30; a flange insertion portion 34 (shown in FIG. 10) extending in an internal direction of the grip 30 from the side surface opening 33; and a flange rotation restricting portion 35 (shown in FIG. 10) that communicates with the flange insertion portion 34, extends into the grip 30, and restricts relative rotation between the grip 30 and the flange 22 that has entered the flange rotation restricting portion 35 by rotating the barrel 20 by a predetermined angle in a state where the flange 22 is housed in the flange insertion portion 34. The flange insertion portion 34 includes a first pair of grip straight portions 36 and 36 having a slightly wider width W1 than the pair of flange straight portions 24 and 24 (width w), and the flange rotation restricting portion 35 includes a second pair of grip straight portions 37 and 37 having a slightly wider width W2 than the pair of flange straight portions 24 and 24 (width w). Thus, the straight line perpendicular distance (W1) between the first pair of grip straight portions 36, 36 is greater than the straight line perpendicular distance (w) between the pair of flange straight portions 24, 24, and the straight line perpendicular distance (W2) between the second pair of grip straight portions 37, 37 is greater than the straight line perpendicular distance (w) between the pair of flange straight portions 24, 24. Each of the second pair of grip straight portions 37 and 37 is inclined (i.e., an angle other than 180°) with respect to a respective one of the first pair of grip straight portions 36 and 36. That is, as shown in FIG. 2, each of the second pair of grip straight portions 37 and 37 is inclined at an angle other than 180° with respect to a respective one of the first pair of grip straight portions 36 and 36.

Figure 10:
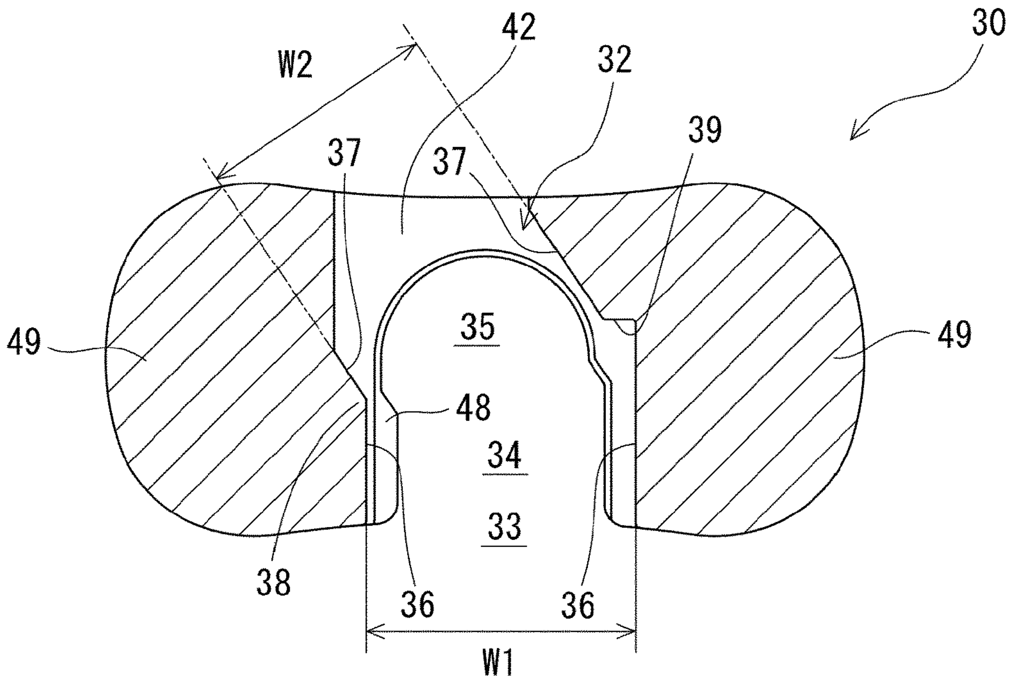
FIG. 10 is a cross-sectional view taken along line X-X in FIG. 7.

In the present embodiment, as illustrated in FIGS. 2, 10, and 12 to 14, at an end portion of the flange insertion portion 34 on the flange rotation restricting portion 35 side, a protrusion 38 is provided that abuts on the flange 22 (flange straight portion 24) when the barrel 20 is rotated and the flange 22 is caused to enter the flange rotation restricting portion 35. As illustrated in FIG. 10, in the grip 30, at an end portion of the left first grip straight portion 36 (in FIG. 10) of the flange insertion portion 34 on the flange rotation restricting portion 35 side (a connecting portion between the left first grip straight portion 36 and the left second grip straight portion 37), the protrusion 38 is formed. That is, the protrusion 38 is located between an end of the left first grip straight portion 36 and an end of the left second grip straight portion 37. In addition, as illustrated in FIG. 10, between the right first grip straight portion 36 (in FIG. 10) and the right second grip straight portion 37, a stepped portion 39 is provided that is continuous to the first grip straight portion 36 at a right angle and connects the first grip straight portion 36 and the second grip straight portion 37 to each other. The stepped portion 39 is thus located between an end of the right first grip straight portion 36 and an end of the right second grip straight portion 37.

Figure 14:
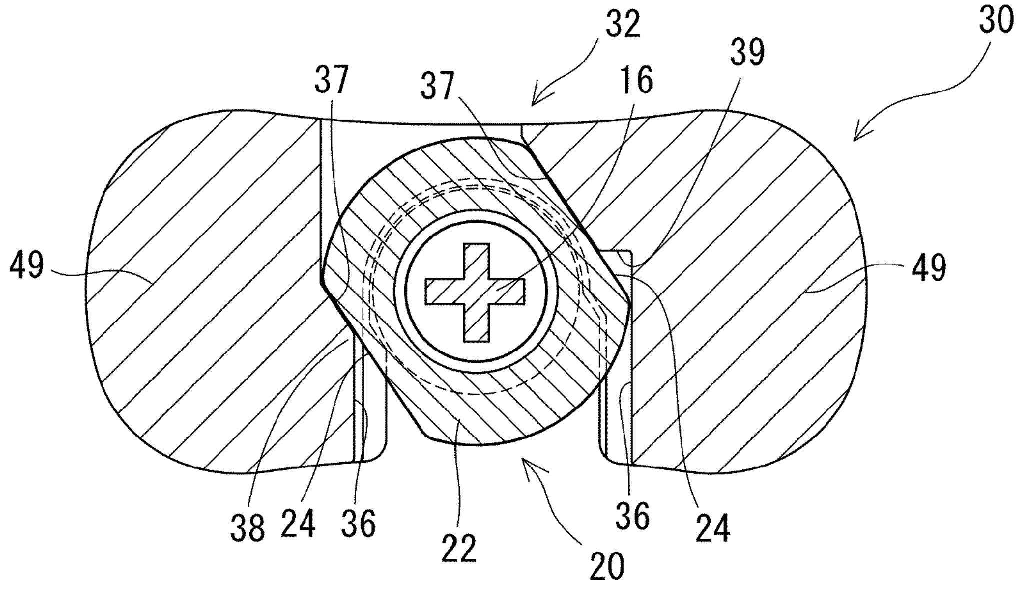
FIG. 14 is a cross-sectional explanatory view corresponding to FIG. 10 for explaining the process for manufacturing the syringe of FIG. 1.

As illustrated in FIGS. 2 and 14, in the grip 30, in a state where the flange 22 is housed in the flange rotation restricting portion 35, front sides of the pair of flange straight portions 24 and 24 are located in the second pair of grip straight portions 37 and 37 (between the second pair of grip straight portions 37 and 37), and rear sides of the pair of flange straight portions 24 and 24 are located in the first pair of grip straight portions 36 and 36 (between the first pair of grip straight portions 36 and 36).

Furthermore, in this embodiment, one rear end portion of the pair of flange straight portions 24 and 24 (an end portion of the flange 22 on a rear side in an insertion direction into the grip 30) abuts on or approaches one of the first pair of grip straight portions 36 and 36. That is, as illustrated in FIGS. 2 and 14, a rear end portion of the right flange straight portion 24 abuts on or approaches the right first grip straight portion 36. As a result, the flange 22 housed in the flange rotation restricting portion 35 is prevented from moving (rattling) along the second pair of grip straight portions 37 and 37 and being detached from the flange rotation restricting portion 35.

Figure 3:
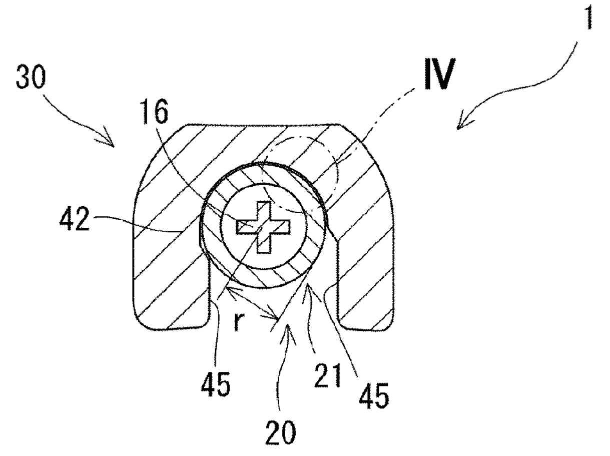
FIG. 3 is a cross-sectional view taken along line III-III in FIG. 1.
Figure 4:
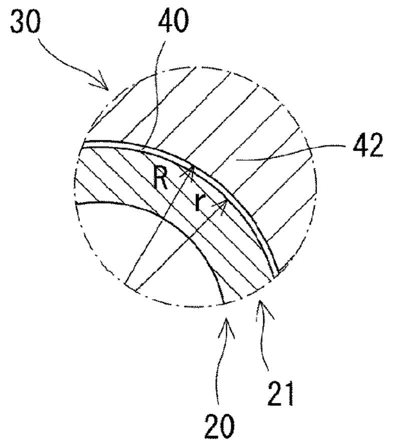
FIG. 4 is an enlarged view of a portion IV in FIG. 3.

As illustrated in FIGS. 3 and 4, in the grip 30, in a state where the flange 22 of the barrel 20 is housed in the flange rotation restricting portion 35 of the grip 30, a lower inner peripheral surface of the grip 30 is not in contact with the barrel 20, and there is a gap 40 for allowing a sterilization gas to flow between the lower inner peripheral surface of the grip 30 and the barrel 20.

Figure 5:
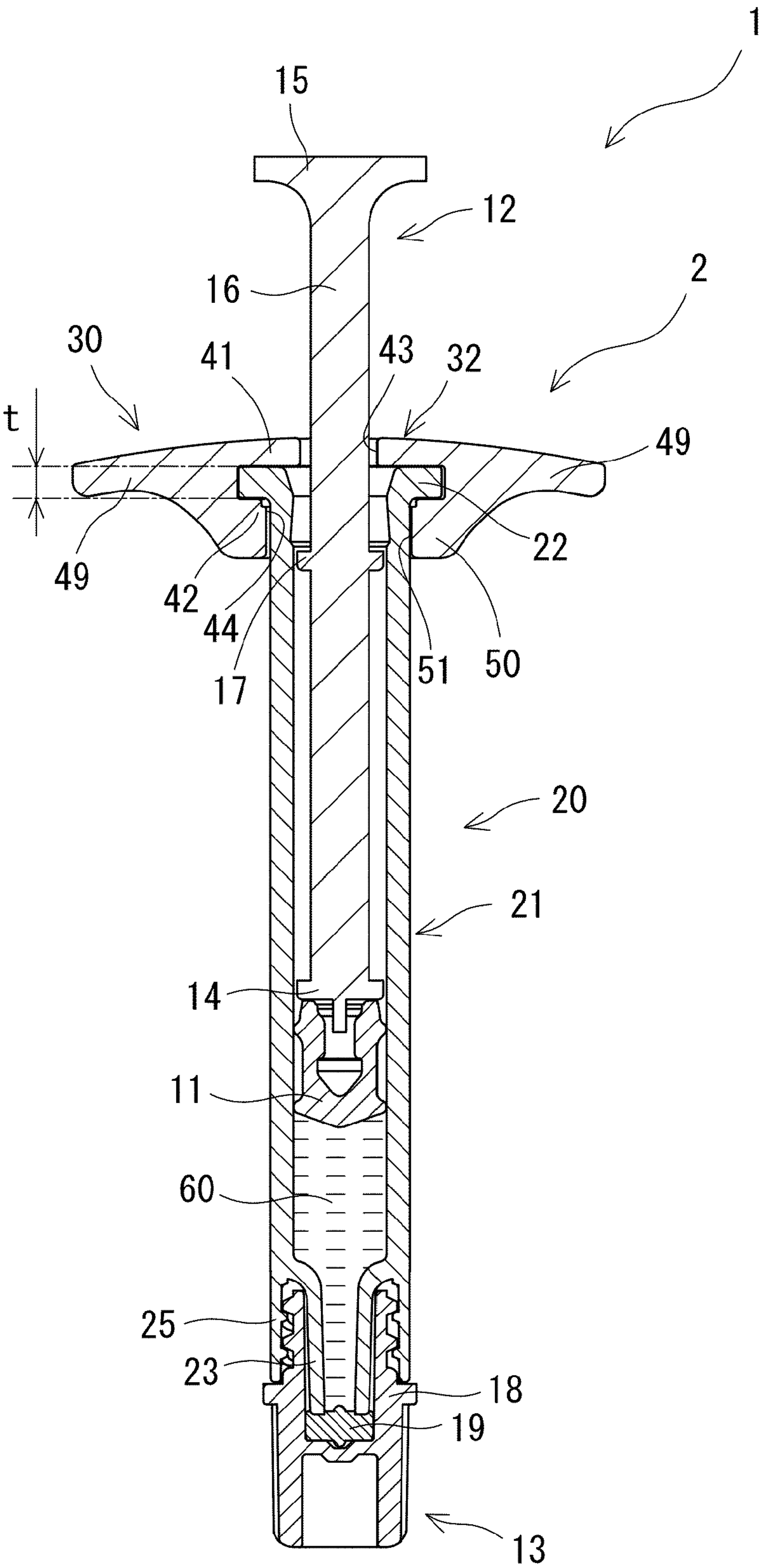
FIG. 5 is a cross-sectional view taken along line V-V in FIG. 2.
Figure 7:
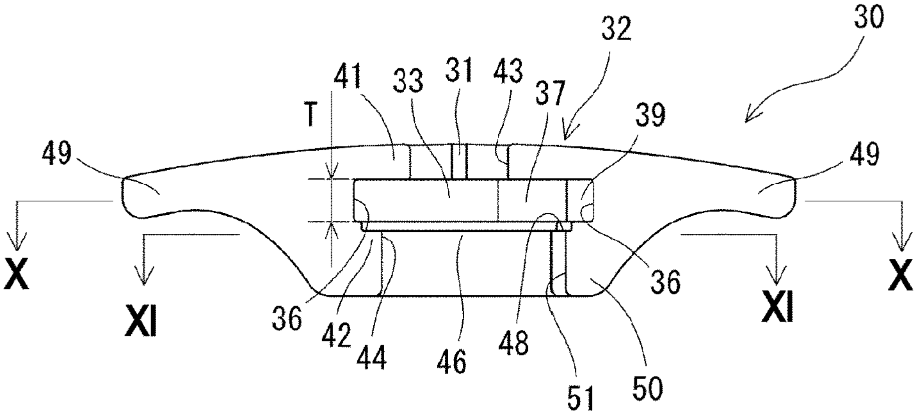
FIG. 7 is a front view of a syringe barrel grip used in the syringe of FIG. 1.

More specifically, as illustrated in FIG. 7, the flange housing portion 32 includes an upper plate portion 41 covering a proximal end side surface of the flange 22 and a lower plate portion 42 covering a distal end side surface of the flange 22. As illustrated in FIGS. 5 and 7, a distance T between the upper plate portion 41 and the lower plate portion 42 of the flange housing portion 32 is larger than the thickness t of the flange 22. As a result, a gap for allowing a sterilization gas to flow is formed between the upper plate portion 41 and the proximal end side surface of the flange 22 and/or between the lower plate portion 42 and the distal end side surface of the flange 22.

Figure 8:
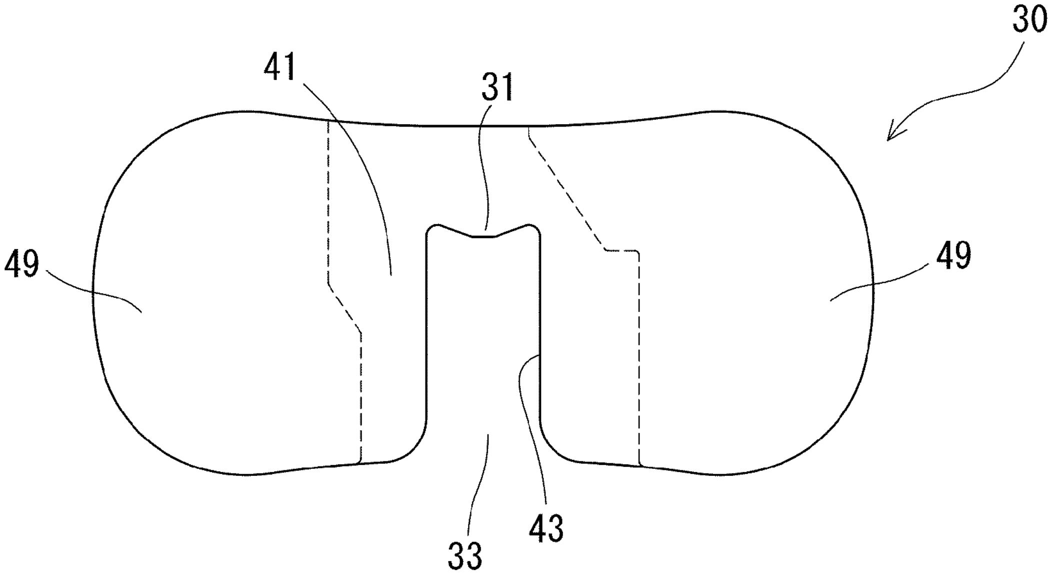
FIG. 8 is a plan view of the syringe barrel grip used in the syringe of FIG. 1.

As illustrated in FIG. 8, an upper slit (opening) 43 is formed in the upper plate portion 41 of the flange housing portion 32. The upper slit 43 communicates with the side surface opening 33, the flange insertion portion 34, and the flange rotation restricting portion 35 of the flange housing portion 32, and is formed such that the shaft portion 16 of the plunger 12 can enter (pass through) the upper slit 43. A part of an inner edge portion of the upper slit 43 is a stopper abutment portion 31 that protrudes inward and abuts on the stopper portion 17 of the plunger 12.

Figure 6:
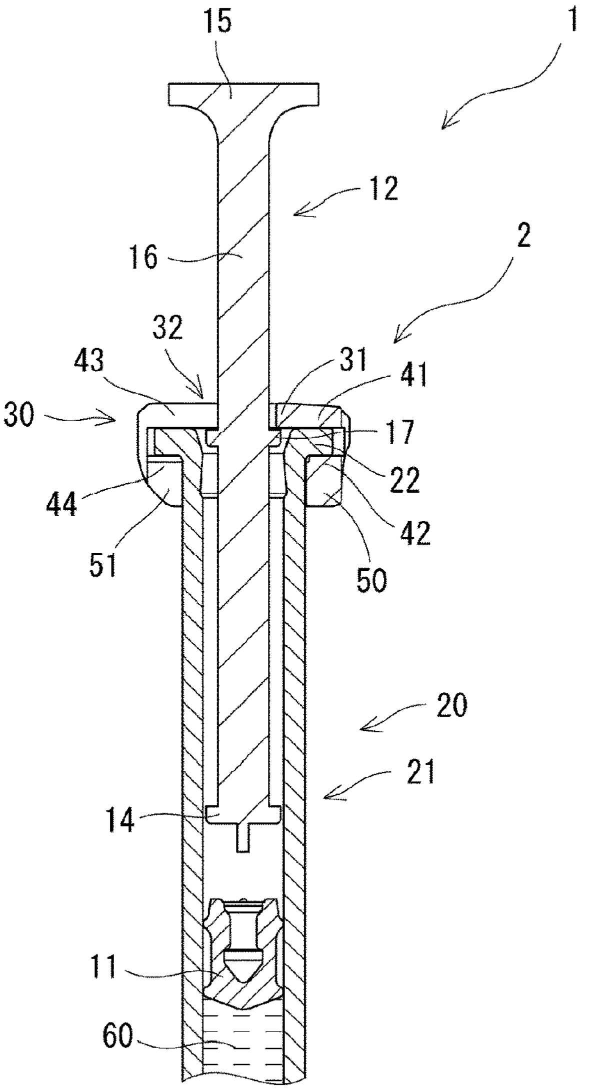
FIG. 6 is an explanatory view for explaining operation of the syringe illustrated in FIG. 1.

As a result, the upper slit 43 allows the shaft portion 16 of the plunger 12 to pass therethrough, and abuts on the stopper portion 17 of the plunger 12 at the stopper abutment portion 31. Therefore, as illustrated in FIG. 6, the plunger 12 housed in the barrel 20 abuts on the stopper abutment portion 31 of the grip 30 at the stopper portion 17, whereby detachment of the plunger 12 from the barrel 20 is restricted.

Figure 9:
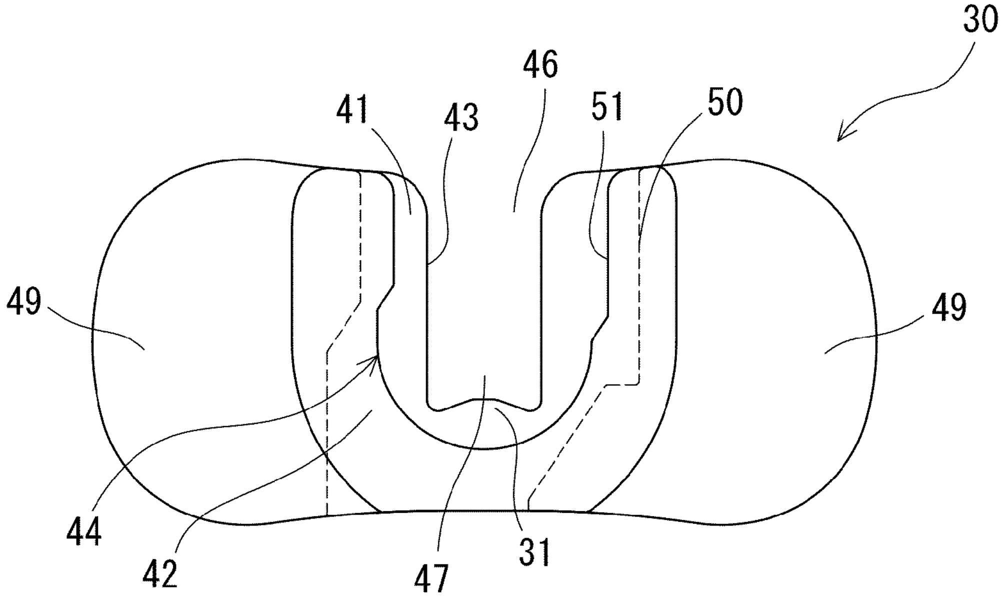
FIG. 9 is a bottom view of the syringe barrel grip used in the syringe of FIG. 1.

As illustrated in FIGS. 9 and 10, a lower slit (opening) 44 is formed in the lower plate portion 42 of the flange housing portion 32. The lower slit 44 communicates with the side surface opening 33, the flange insertion portion 34, and the flange rotation restricting portion 35 of the flange housing portion 32, and is formed such that the cylindrical body 21 of barrel 20 can enter (pass through) the lower slit 44. More specifically, as shown in FIGS. 9-11, the lower plate portion 42 (lower slit 44) includes a barrel insertion portion 46 including a pair of lower straight portions 45 and 45 that has a width W3 larger (wider) than the outer shape (outer diameter) of the barrel 20 (cylindrical body 21) portion that enters the lower slit 44 and narrower than the width w of the pair of flange straight portions 24 and 24, and are substantially parallel to the first pair of grip straight portions 36 and 36, respectively.

Figure 11:
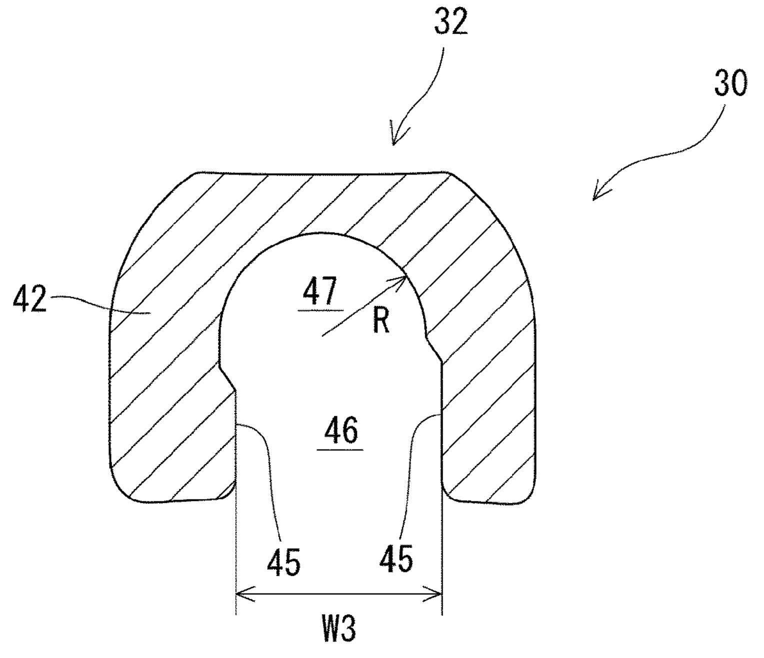
FIG. 11 is a cross-sectional view taken along line XI-XI in FIG. 7.

As illustrated in FIG. 11, the lower plate portion 42 (lower slit 44) includes a barrel housing portion 47 that communicates with the barrel insertion portion 46, and partially surrounds the barrel 20 (cylindrical body 21) (houses the barrel 20) in a state where the flange 22 is housed in the flange rotation restricting portion 35. The barrel housing portion 47 has an inner shape (inner diameter, radius R illustrated in FIG. 11) larger than the outer shape (outer diameter, radius r illustrated in FIG. 3) of the barrel 20 (cylindrical body 21) housed therein. As a result, as illustrated in FIG. 3, in a state where the flange 22 is housed in the flange rotation restricting portion 35 of the grip 30, an inner peripheral surface of the barrel housing portion 47 is not in contact with the barrel 20, and the gap 40 for allowing a sterilization gas to flow between the inner peripheral surface of the barrel housing portion 47 and the barrel 20 is formed. That is, in the grip 30, on an inner peripheral surface of the lower plate portion 42 of the flange housing portion 32 (the barrel housing portion 47 of the lower slit 44), at least a part of a lower inner peripheral surface of the grip 30 is formed.

As illustrated in FIGS. 7 and 10, a recess 48 is formed in an upper inner edge portion of the lower plate portion 42. As a result, a sterilization gas can be brought into contact with a wider area of a distal end side surface of the flange 22 facing the lower plate portion 42.

In the flange housing portion 32 of the grip 30, a pair of finger hook portions 49 and 49 is formed so as to constitute a proximal end side portion of the grip 30 and to protrude outward (in a direction orthogonal to the axial direction of the barrel 20). The pair of finger hook portions 49 and 49 protrude in directions opposite to each other and orthogonal to the axial direction of the barrel 20. The pair of finger hook portions 49 and 49 extends outward from the flange 22 of the barrel 20. The pair of finger hook portions 49 and 49 can be used by an operator to hook a finger when the operator operates the syringe 1.

As illustrated in FIGS. 5 and 7, the grip 30 of the present embodiment includes a side wall portion 50 extending to an axial distal end side from the flange housing portion 32. The side wall portion 50 is integrated with (connected to) an inner edge portion of the lower slit 44 of the lower plate portion 42 of the flange housing portion 32 at a proximal end thereof. As illustrated in FIG. 7, the outer shape of the side wall portion 50 increases toward a proximal end side (flange housing portion 32 side), and is smoothly connected to the finger hook portions 49 and 49 of the flange housing portion 32. As a result, the side wall portion 50 contributes to improvement in operability of the syringe 1.

An inner peripheral surface of the side wall portion 50 is formed by extending an inner peripheral surface of the lower slit 44 in the axial direction over the entire length in the axial direction, and has a semi-cylindrical shape with a substantially U-shaped cross section as a whole. In the side wall portion 50, an opening for insertion extending over the entire length in the axial direction (for insertion of a proximal end portion of the cylindrical body 21) (insertion slit) 51 is formed. In a state where the flange 22 of the barrel 20 is housed in the flange rotation restricting portion 35 of the grip 30, an inner peripheral surface of the side wall portion 50 is not in contact with the barrel 20, and a gap for allowing a sterilization gas to flow between the inner peripheral surface of the side wall portion 50 and the barrel 20 (the gap 40 and a gap continuous with the gap 40) is formed. In other words, the side wall portion 50 partially covers a proximal end portion of the cylindrical body 21 adjacent to the flange 22, and at least a part of the inner peripheral surface constitutes a lower inner peripheral surface of the grip 30 that forms a gap for allowing a sterilization gas to flow between the inner peripheral surface and the barrel 20.

Preferable examples of a constituent material from which the grip 30 may be fabricated include a hard or semi-hard resin such as a polyolefin including polyethylene and polypropylene, polystyrene, polyamide, polycarbonate, polyvinyl chloride, poly-(4-methylpentene-1), an acrylic resin, an acrylonitrile-butadiene-styrene copolymer, a polyester including polyethylene terephthalate, a cyclic polyolefin polymer, or a cyclic olefin copolymer.

As a constituent material from which the grip 30 may be fabricated, a material having a thermal expansion coefficient (linear thermal expansion coefficient) larger than that of the barrel 20 may be used. As a result, when the syringe 1 is heated in a surface sterilization (gas sterilization) step described later, an inner surface (inner diameter) of the grip 30 expands more than an outer surface (outer diameter) of the barrel 20 (cylindrical body 21), a gap is formed or expanded between the inner surface of the grip 30 and the outer surface of the cylindrical body 21, and a sterilization gas enters the gap, whereby sterilizability of the syringe 1 can be improved.

A method (process) for manufacturing such a syringe 1 will be described.

First, the barrel 20 is sterilized with the seal cap 13 attached to the nozzle portion 23 of the barrel 20. A sterilization method adopted at this time is not particularly limited, and for example, an autoclave sterilization method using an autoclave (high temperature steam sterilization method), a surface sterilization method using a sterilization gas such as hydrogen peroxide or EOG (gas sterilization method), or a radiation sterilization method by radiation irradiation using a y ray, an electron radiation, or the like can be used. Here, as an example, autoclave sterilization is performed.

Subsequently, under a sterile environment, the drug 60 that has been previously subjected to sterilization treatment (for example, filtration sterilization) is aseptically filled in the sterilized barrel 20. In the present embodiment, the drug 60 for ophthalmic use, which is relatively vulnerable to heat, is filled. After the drug 60 is filled, the gasket 11 is inserted into the barrel 20. The gasket 11 can be inserted (capped) in a depressurized state.

Subsequently, a distal end side portion of the plunger 12 is housed in the barrel 20, and the grip 30 is attached to the barrel 20. This operation can also be performed under an environment other than a sterile environment.

A step of attaching the grip 30 to the barrel 20 will be described in detail with reference to FIGS. 12 to 14.

Figure 12:
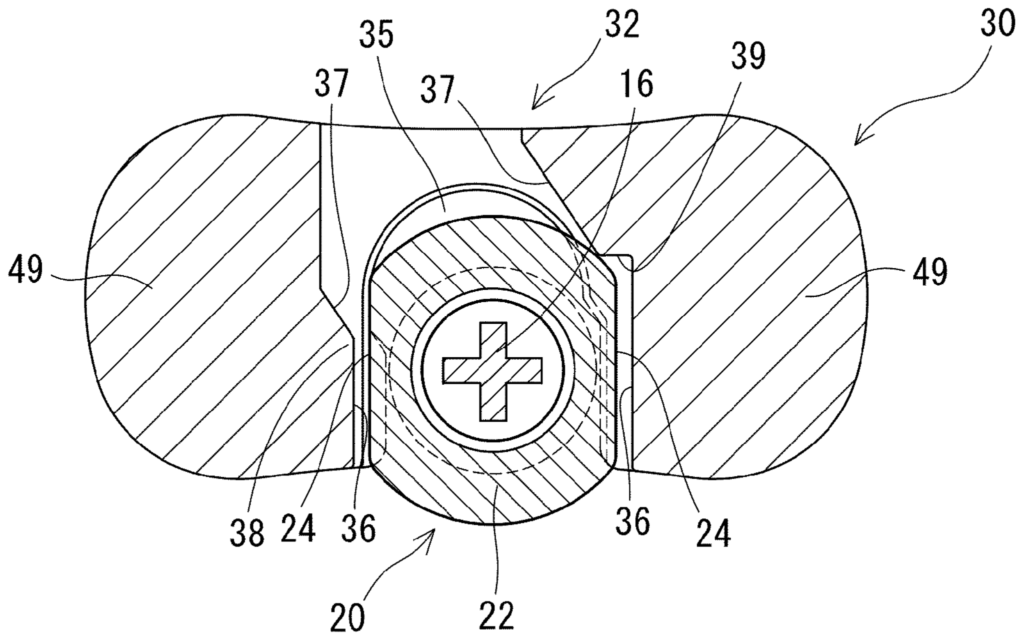
FIG. 12 is a cross-sectional explanatory view corresponding to FIG. 10 for explaining a process for manufacturing the syringe of FIG. 1.
Figure 13:
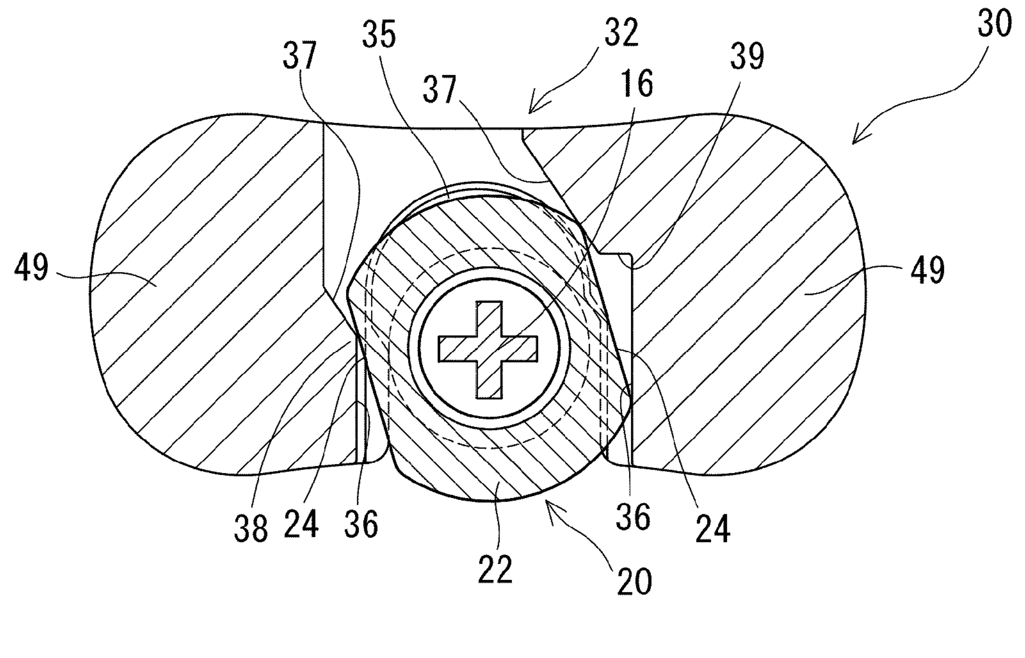
FIG. 13 is a cross-sectional explanatory view corresponding to FIG. 10 for explaining the process for manufacturing the syringe of FIG. 1.

First, as illustrated in FIG. 12, in a state where the pair of flange straight portions 24 and 24 of the barrel 20 and the first pair of grip straight portions 36 and 36 of the grip 30 are substantially parallel to each other, the flange 22 of the barrel 20 is inserted into the grip 30 from the side surface opening 33, and the flange 22 is housed in the flange insertion portion 34.

Subsequently, in a state where the flange 22 is housed in the flange insertion portion 34, the barrel 20 is biased in a rotational direction (here, counterclockwise) and rotated (rotated relative to the grip 30). During the rotation of the barrel 20, as illustrated in FIG. 13, one (here, the left flange straight portion 24 in FIG. 13) of the pair of flange straight portions 24 and 24 abuts on the protrusion 38, and a rear end portion of the other (here, the right flange straight portion 24 in FIG. 13) or a portion in the vicinity thereof abuts on the right first grip straight portion 36 in FIG. 13 [the grip 30 (flange housing portion 32) and barrel 20 (flange 22) are temporarily engaged with each other (first engagement state)].

When the barrel 20 is further biased in the rotational direction from the state where the grip 30 and the barrel 20 are engaged with each other, the upper slit 43, the lower slit 44, and the insertion slit 51 are formed in the grip 30 (the flange housing portion 32 and the side wall portion 50), and therefore the flange housing portion 32 of the grip 30 is elastically deformed and pushed out. As a result, the rotation of the barrel 20 is allowed, the engagement state between the barrel 20 (flange 22) and the grip 30 (flange housing portion 32) is released, and the flange 22 enters the flange rotation restricting portion 35. That is, the grip 30 is temporarily engaged with the barrel 20 when the flange 22 is caused to enter the flange rotation restricting portion 35 by rotating the barrel 20 by a predetermined angle in a state where the flange 22 is housed in the flange insertion portion 34.

As illustrated in FIG. 14, when the flange 22 is housed in the flange rotation restricting portion 35 (the grip 30 is attached to the barrel 20), the grip 30 returns to the original state by an elastic restoring force. That is, portions of the flange housing portion 32 that are elastically deformed and pushed out so that the flange 22 is able to enter the flange rotation restricting portion 35 return to their original state by an elastic restoring force. By causing the flange 22 to enter the flange rotation restricting portion 35, the attachment of the grip 30 to the barrel 20 is completed. In a state where the flange 22 is housed in the flange rotation restricting portion 35, the pair of flange straight portions 24 and 24 face the second pair of grip straight portions 37 and 37, respectively, whereby relative rotation between the barrel 20 and the grip 30 is restricted.

When the barrel 20 is biased in a rotational direction (here, clockwise) opposite to the rotational direction when the flange 22 is caused to enter the flange rotation restricting portion 35 in a state where the grip 30 is attached, one (here, the left flange straight portion 24 in FIG. 14) of the pair of flange straight portions 24 and 24 abuts on the protrusion 38, and a front end portion of the other (here, the right flange straight portion 24 in FIG. 14) or a portion in the vicinity thereof abuts on the right second grip straight portion 37 in FIG. 14 [the grip 30 (flange housing portion 32) and barrel 20 (flange 22) are temporarily engaged with each other (second engagement state)]. Therefore, it is possible to prevent the grip 30 attached to the barrel 20 from unintentionally falling off. In other words, since the grip 30 is temporarily engaged with the barrel 20 (the first engagement state exists) when the flange 22 is caused to enter the flange rotation restricting portion 35 by rotating the barrel 20 by a predetermined angle in a state where the flange 22 is housed in the flange insertion portion 34, the second engagement state occurs in the flange 22 once housed in the flange pivoting restriction portion 35, and detachment of the grip 30 from the barrel 20 after attachment can be prevented.

Subsequently, the syringe 1 with the grip 30 attached to the barrel 20 is sterilized. In the present embodiment, since the drug 60 stored in the barrel 20 is a drug for ophthalmic use, which is relatively vulnerable to heat, surface sterilization ($NO_2$ sterilization) using a sterilization gas (here, $NO_2$ (nitrogen dioxide)) is performed.

As described above, the syringe 1 can be aseptically manufactured.

The grip 30 (flange housing portion 32) of the present embodiment includes the flange rotation restricting portion 35 including the second pair of grip straight portions 37 and 37 that is inclined with respect to the first pair of grip straight portions 36 and 36 disposed in the flange insertion portion 34, and in a state where the flange 22 is stored in the flange rotation restricting portion 35, a part of the pair of flange straight portions 24 and 24 is located in the second pair of grip straight portions 37 and 37. Therefore, relative rotation between the flange 22 (barrel 20) and the grip 30 is restricted in a state where the grip 30 is attached to the syringe barrel 20, and therefore operability is good.

Furthermore, in the grip 30 of the present embodiment, in a state where the flange 22 of the barrel 20 is housed in the flange rotation restricting portion 35 of the grip 30, a lower inner peripheral surface of the grip 30 (an inner peripheral surface of the lower slit 44 of the lower plate portion 42 and/or an inner peripheral surface of the side wall portion 50) is not in contact with the barrel 20, and there is a gap 40 for allowing a sterilization gas to flow between the lower inner peripheral surface of the grip 30 and the barrel 20. Therefore, the sterilization gas can be brought into contact with a wider area of surfaces of the grip 30 and the barrel 20, and the syringe barrel grip 30 and the syringe barrel 20 to which such a grip 30 is attached are more reliably sterilized.

In the present embodiment, the cylindrical body 21 of the barrel 20 has a circular cylindrical shape in which the cross sections of the outer shape and the inner shape are substantially circular, but the present invention is not limited thereto. It is possible to appropriately use those having various cylindrical shapes in which the cross sections are elliptical, polygonal, and the like, those having different cross-sectional shapes between the outer shape and the inner shape, and the like, and the shape of the grip 30 (flange housing portion 32) can also be appropriately changed accordingly.

Figure 15:
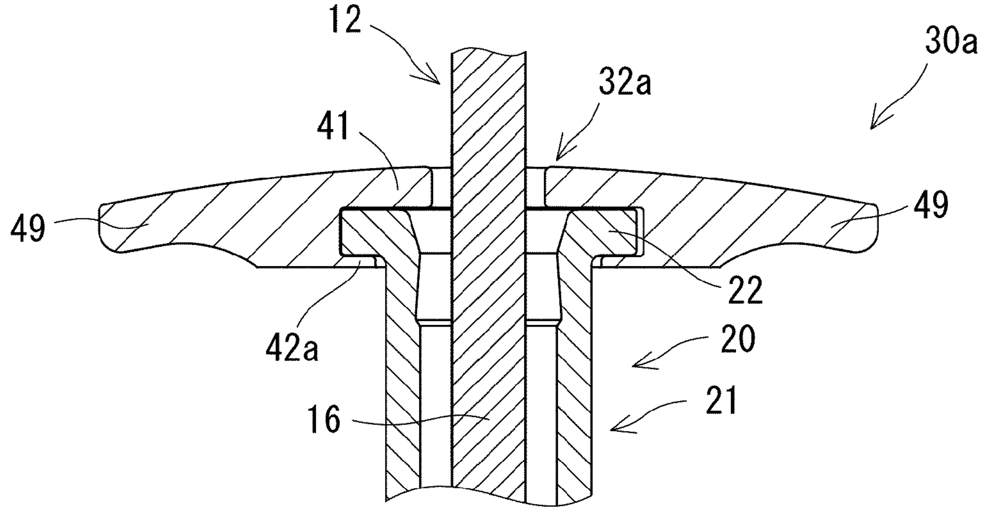
FIG. 15 is a cross-sectional partial explanatory view corresponding to FIG. 5 for explaining a syringe barrel grip according to another embodiment.

In addition, as in a grip 30*a* illustrated in FIG. 15, the side wall portion (50) does not have to be disposed. In the grip 30*a*, a lower plate portion 42*a* of a flange housing portion

32*a* constitutes a most distal end portion (lowest portion) of the grip 30*a*. As a result, the grip 30*a* can be further reduced in size and weight.

Figure 16:
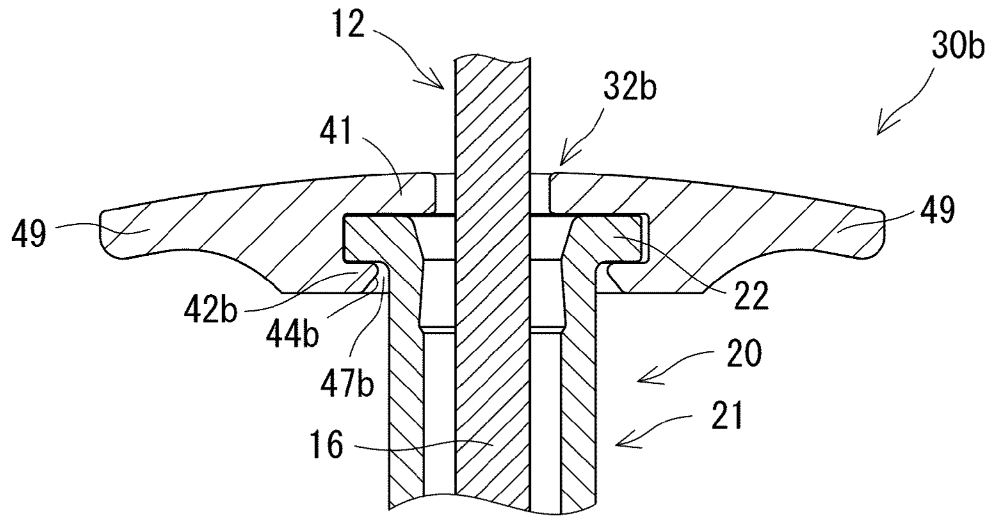
FIG. 16 is a cross-sectional partial explanatory view corresponding to FIG. 5 for explaining a syringe barrel grip according to another embodiment.

In a grip 30*b* illustrated in FIG. 16, a lower plate portion 42*b* of a flange housing portion 32*b* is thicker than the grip 30*a* (lower plate portion 42*a*) described above. As a result, the strength of the grip 30*b* can be increased. In the grip 30*b*, as illustrated in FIG. 16, an inner peripheral surface (inner shape) of the lower plate portion 42*b* (a barrel housing portion 47*b* of a lower slit 44*b*) expands downward. As a result, a flow of a sterilization gas between the grip 30*b* and the barrel 20 is further promoted while the strength of the grip 30*b* is increased by thickening the lower plate portion 42*b*, and the sterilization is more reliably performed.

Figure 17:
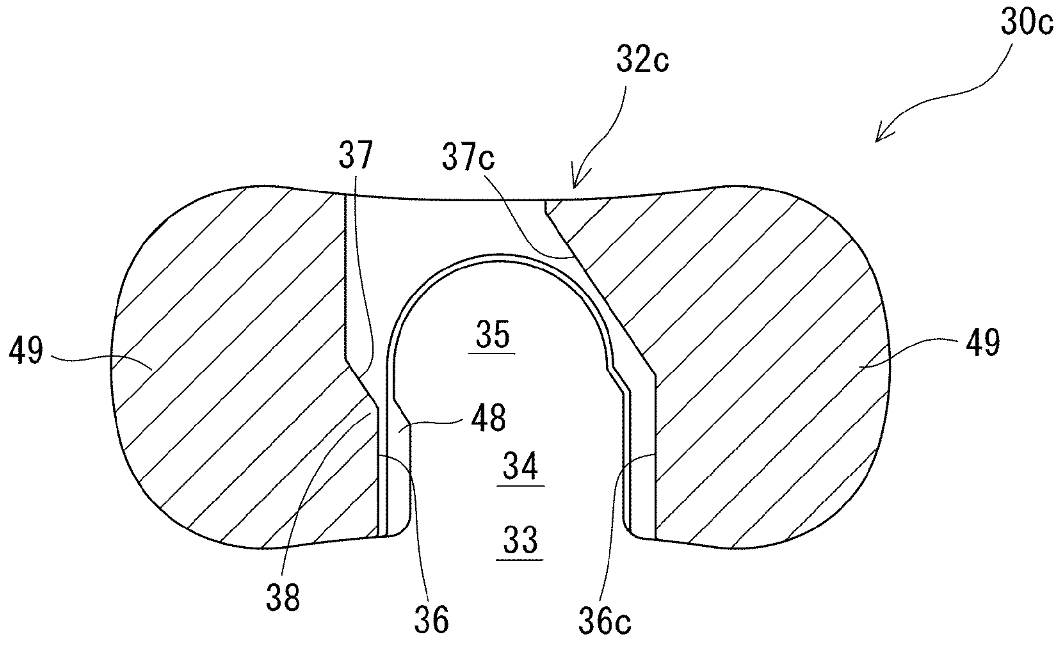
FIG. 17 is a cross-sectional explanatory view corresponding to FIG. 10 for explaining a syringe barrel grip according to another embodiment.

In addition, as in a grip 30*c* illustrated in FIG. 17, a right first grip straight portion 36*c* and a right second grip straight portion 37*c* in FIG. 17 in a flange housing portion 32*c* may be connected to each other directly without forming the stepped portion 39.

Figure 18:
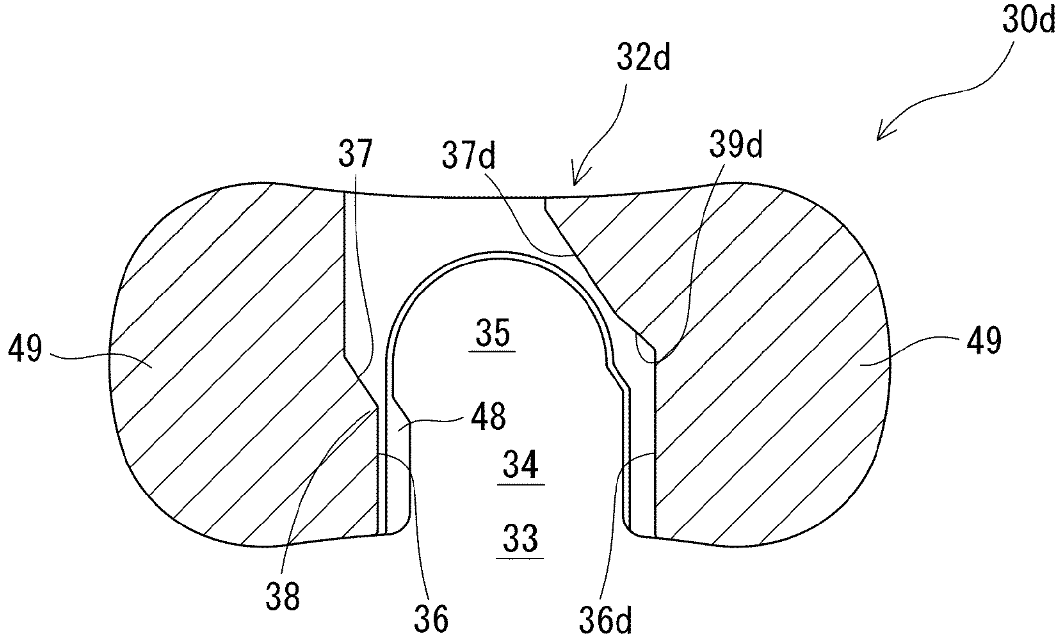
FIG. 18 is a cross-sectional explanatory view corresponding to FIG. 10 for explaining a syringe barrel grip according to another embodiment.

In addition, as in a grip 30*d* illustrated in FIG. 18, a right first grip straight portion 36*d* and a right second grip straight portion 37*d* in FIG. 18 in a flange housing portion 32*d* may be connected to each other at a gentle angle with an inclined stepped portion 39*d*.

In addition, although not illustrated, the protrusion 38 formed in the flange housing portion 32 is not limited to the one illustrated by way of example. For example, the protrusion 38 may be formed so as to protrude from the first grip straight portion 36 toward the inside of the flange housing portion 32, and as for a formation portion thereof, the protrusion 38 may be formed at a middle portion of the first grip straight portion 36 instead of the end portion of the first grip straight portion 36 on the flange rotation restricting portion 35 side.

The syringe barrel grip disclosed by way of example here includes feature like the following.

(1) A syringe barrel grip attached to a syringe barrel including a cylindrical body and a flange disposed in the cylindrical body, protruding outward, and including a pair of flange straight portions facing each other in parallel, the grip including a flange housing portion that houses the flange, in which the flange housing portion includes: a side surface opening formed on a side surface of the grip; a flange insertion portion extending in an internal direction of the grip from the side surface opening; and a flange rotation restricting portion that communicates with the flange insertion portion, extends into the grip, and restricts relative rotation between the grip and the flange that has entered the flange rotation restricting portion by rotating the barrel by a predetermined angle in a state where the flange is housed in the flange insertion portion, the flange insertion portion includes a first pair of grip straight portions having a slightly wider width than the pair of flange straight portions, and the flange rotation restricting portion includes a second pair of grip straight portions having a slightly wider width than the pair of flange straight portions and is inclined with respect to the first pair of grip straight portions, in a state where the flange is housed in the flange rotation restricting portion, front sides of the pair of flange straight portions are located in the second pair of grip straight portions, and rear sides of the pair of flange straight portions are located in the first pair of grip straight portions, and in a state where the flange of the barrel is housed in the flange rotation restricting portion of the grip, a lower inner peripheral surface of the grip is not in contact with the barrel, and there is a gap for allowing a sterilization gas to flow between the lower inner peripheral surface of the grip and the barrel.

The syringe barrel grip is attached to a syringe barrel including a cylindrical body and a flange disposed in the cylindrical body, protruding outward, and including a pair of flange straight portions facing each other in parallel. The grip includes a flange housing portion that houses a flange, and the flange housing portion includes: a side surface opening formed on a side surface of the grip; a flange insertion portion extending in an internal direction of the grip from the side surface opening; and a flange rotation restricting portion that communicates with the flange insertion portion, extends into the grip, and restricts relative rotation between the grip and the flange that has entered the flange rotation restricting portion by rotating the barrel by a predetermined angle in a state where the flange is housed in the flange insertion portion.

Furthermore, the flange insertion portion of the grip includes a first pair of grip straight portions having a slightly wider width than the pair of flange straight portions, the flange rotation restricting portion includes a second pair of grip straight portions having a slightly wider width than the pair of flange straight portions and is inclined with respect to the first pair of grip straight portions, and in a state where the flange is housed in the flange rotation restricting portion, front sides of the pair of flange straight portions are located in the second pair of grip straight portions, and rear sides of the pair of flange straight portions are located in the first pair of grip straight portions.

Therefore, in the syringe barrel grip, the barrel assembly, and the syringe disclosed by way of example here, relative rotation between the flange and the grip is restricted in a state where the grip is attached to the syringe barrel, and therefore operability is good.

Furthermore, in the grip, in a state where the flange of the barrel is housed in the flange rotation restricting portion of the grip, a lower inner peripheral surface of the grip is not in contact with the barrel, and there is a gap for allowing a sterilization gas to flow between the lower inner peripheral surface of the grip and the barrel.

Therefore, in the syringe barrel grip, the barrel assembly, and the syringe, the sterilization gas can be brought into contact with a wider area of surfaces of the grip and the barrel, and the syringe barrel grip and a syringe barrel to which such a grip is attached are more reliably sterilized.

In addition, the above embodiment may be as follows.

(2) The syringe barrel grip according to (1), in which the grip includes a side wall portion partially covering a proximal end portion of the cylindrical body adjacent to the flange, and at least a part of an inner peripheral surface of the side wall portion is the lower inner peripheral surface.

(3) The syringe barrel grip according to (1) or (2), in which the grip is temporarily engaged with the barrel when the flange is caused to enter the flange rotation restricting portion by rotating the barrel by a predetermined angle in a state where the flange is housed in the flange insertion portion.

(4) The syringe barrel grip according to any one of (1) to (3), in which the flange housing portion includes an upper plate portion covering a proximal end side surface of the flange and a lower plate portion covering a distal end side surface of the flange, a distance between the upper plate portion and the lower plate portion is larger than the thickness of the flange, and a gap for allowing a sterilization gas to flow is formed between the upper plate portion and the proximal end side surface of the flange and/or between the lower plate portion and the distal end side surface of the flange.

The barrel assembly disclosed by way of example here includes feature like the following.

(5) A barrel assembly including: a syringe barrel including a cylindrical body and a flange disposed at a proximal end of the cylindrical body, protruding outward, and including a pair of flange straight portions facing each other in parallel; and the syringe barrel grip according to any one of (1) to (4) attached to the barrel.

The barrel assembly o includes a syringe barrel grip attached to a syringe barrel including a cylindrical body and a flange disposed in the cylindrical body, protruding outward, and including a pair of flange straight portions facing each other in parallel. The grip includes a flange housing portion that houses a flange, and the flange housing portion includes: a side surface opening formed on a side surface of the grip; a flange insertion portion extending in an internal direction of the grip from the side surface opening; and a flange rotation restricting portion that communicates with the flange insertion portion, extends into the grip, and restricts relative rotation between the grip and the flange that has entered the flange rotation restricting portion by rotating the barrel by a predetermined angle in a state where the flange is housed in the flange insertion portion.

Furthermore, the flange insertion portion of the grip includes a first pair of grip straight portions having a slightly wider width than the pair of flange straight portions, the flange rotation restricting portion includes a second pair of grip straight portions having a slightly wider width than the pair of flange straight portions and is inclined with respect to the first pair of grip straight portions, and in a state where the flange is housed in the flange rotation restricting portion, front sides of the pair of flange straight portions are located in the second pair of grip straight portions, and rear sides of the pair of flange straight portions are located in the first pair of grip straight portions.

Therefore, in the barrel assembly, relative rotation between the flange and the grip is restricted in a state where the grip is attached to the syringe barrel, and therefore operability is good.

Furthermore, in the barrel assembly, in a state where the flange of the barrel is housed in the flange rotation restricting portion of the grip, a lower inner peripheral surface of the grip is not in contact with the barrel, and there is a gap for allowing a sterilization gas to flow between the lower inner peripheral surface of the grip and the barrel.

Therefore, in the barrel assembly, the sterilization gas can be brought into contact with a wider area of surfaces of the grip and the barrel, and the syringe barrel grip and a syringe barrel to which such a grip is attached are more reliably sterilized.

The syringe disclosed by way of example here includes feature like the following.

(6) A syringe including: the barrel assembly according to (5); a gasket slidably housed in the barrel; and a plunger for moving the gasket.

The syringe includes a syringe barrel grip attached to a syringe barrel including a cylindrical body and a flange disposed in the cylindrical body, protruding outward, and including a pair of flange straight portions facing each other in parallel. The grip includes a flange housing portion that houses a flange, and the flange housing portion includes: a side surface opening formed on a side surface of the grip; a flange insertion portion extending in an internal direction of the grip from the side surface opening; and a flange rotation restricting portion that communicates with the flange insertion portion, extends into the grip, and restricts relative rotation between the grip and the flange that has entered the flange rotation restricting portion by rotating the barrel by a predetermined angle in a state where the flange is housed in the flange insertion portion.

Furthermore, the flange insertion portion of the grip includes a first pair of grip straight portions having a slightly wider width than the pair of flange straight portions, the flange rotation restricting portion includes a second pair of grip straight portions having a slightly wider width than the pair of flange straight portions and is inclined with respect to the first pair of grip straight portions, and in a state where the flange is housed in the flange rotation restricting portion, front sides of the pair of flange straight portions are located in the second pair of grip straight portions, and rear sides of the pair of flange straight portions are located in the first pair of grip straight portions.

Therefore, the syringe is configured so that relative rotation between the flange and the grip is restricted in a state where the grip is attached to the syringe barrel, and therefore operability is good.

Furthermore, in the disclosed syringe, in a state where the flange of the barrel is housed in the flange rotation restricting portion of the grip, a lower inner peripheral surface of the grip is not in contact with the barrel, and there is a gap for allowing a sterilization gas to flow between the lower inner peripheral surface of the grip and the barrel.

Therefore, the sterilization gas can be brought into contact with a wider area of surfaces of the grip and the barrel, and the syringe barrel grip and a syringe barrel to which such a grip is attached are more reliably sterilized.

In addition, the above embodiment may be as follows.

(7) The syringe according to (6), in which a distal end side portion of the plunger is housed in the barrel, and the plunger includes a stopper portion that is disposed in a portion housed in the barrel, abuts on the grip, and restricts detachment of the plunger from the barrel.

(8) The syringe according to (6) or (7), in which the plunger is not connected to the gasket and includes a gasket pressing portion that abuts on a proximal end portion of the gasket at a distal end thereof.

(9) The syringe according to any one of (6) to (8), in which a drug is stored in the barrel.

The detailed description above describes embodiments of a syringe barrel grip attached to a syringe barrel, and a barrel assembly and syringe each including the syringe barrel grip, representing examples of the new syringe barrel grip, barrel assembly and syringe disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe barrel grip configured to be attached to a syringe barrel, the syringe barrel including a cylindrical body and a flange disposed on the cylindrical body, the flange protruding outward from the cylindrical body and including a pair of flange straight portions parallel to one another and spaced apart from one another by a first width, the syringe barrel grip comprising:

a flange housing portion configured to house the flange of the syringe barrel when the syringe barrel grip is attached to the syringe barrel;

the flange housing portion including: a side surface opening formed on a side surface of the syringe barrel grip through which the flange of the syringe barrel is configured to pass as the flange of the syringe is being housed in the flange housing portion; a flange insertion portion extending in an internal direction of the syringe barrel grip from the side surface opening and configured to receive the flange of the syringe barrel that has passed through the side surface opening; and a flange rotation restricting portion that communicates with the flange insertion portion, extends into the syringe barrel grip, receives the flange of the syringe barrel as a result of relative rotation between the flange of the syringe barrel and the syringe barrel grip when the flange of the syringe barrel is positioned in the flange insertion portion, and restricts relative rotation between the syringe barrel grip and the flange of the syringe barrel after the flange of the syringe barrel is positioned in the flange rotation restricting portion;

the flange insertion portion including a first pair of grip straight portions spaced apart from one another by a second width that is greater than the first width, and the flange rotation restricting portion including a second pair of grip straight portions spaced apart from one another by a third width that is greater than the first width, each of the second pair of grip straight portions being inclined with respect to a respective one of the first pair of grip straight portions;

the flange rotation restricting portion being configured such that when the flange of the syringe barrel is positioned in the flange rotation restricting portion, front sides of the pair of flange straight portions are located between the second pair of grip straight portions, and rear sides of the pair of flange straight portions are located between the first pair of grip straight portions; and the flange rotation restricting portion of the flange housing portion being configured such that when the flange of the syringe barrel is positioned in the flange rotation restricting portion, a lower inner peripheral surface of the syringe barrel grip is not in contact with the barrel so that a gap exists between the lower inner peripheral surface of the syringe barrel grip and the barrel, the gap allowing a sterilization gas to flow between the lower inner peripheral surface of the grip and the barrel.

2. The syringe barrel grip configured to be attached to the syringe barrel according to claim 1, wherein the grip includes a side wall portion configured to partially cover a proximal end portion of the cylindrical body adjacent to the flange, and at least a part of an inner peripheral surface of the side wall portion is the lower inner peripheral surface of the grip.

3. The syringe barrel grip configured to be attached to the syringe barrel according to claim 1, wherein the flange is configured to be positioned in the flange rotation restricting portion of the flange housing portion by passing the flange through the side surface opening to temporarily position the flange in the flange insertion portion and then rotating the barrel by a predetermined angle to cause the flange that is temporarily positioned in the flange insertion portion to enter the flange rotation restricting portion.

4. The syringe barrel grip configured to be attached to the syringe barrel according to claim 1, wherein the flange housing portion includes an upper plate portion configured to cover a proximal end side surface of the flange and a lower plate portion configured to cover a distal end side surface of the flange when the flange of the syringe barrel is positioned in the flange rotation restricting portion, a distance between the upper plate portion and the lower plate portion being configured to be larger than a thickness of the flange as measured between the proximal end side surface of the flange and the distal end side surface of the flange so that a gap exists allowing a sterilization gas to flow between the upper plate portion and the proximal end side surface of the flange and/or between the lower plate portion and the distal end side surface of the flange when the flange of the syringe barrel is positioned in the flange rotation restricting portion.

5. The syringe barrel grip configured to be attached to the syringe barrel according to claim 1, wherein one of the first pair of grip straight portions along one side of the flange insertion portion and one of the second pair of grip straight portions along the one side of the flange insertion portion are separated from each other by a protrusion.

6. The syringe barrel grip configured to be attached to the syringe barrel according to claim 5, wherein the other one of the first pair of grip straight portions along an other side of the flange insertion portion and the other one of the second pair of grip straight portions along the other side of the flange insertion portion are separated from each other by a stepped portion.

7. The syringe barrel grip configured to be attached to the syringe barrel according to claim 5, wherein the other one of the first pair of grip straight portions along an other side of the flange insertion portion and the other one of the second pair of grip straight portions along the other side of the flange insertion portion are directly connected to one another.

8. The syringe barrel grip configured to be attached to the syringe barrel according to claim 1, wherein the flange housing portion includes an upper plate portion configured to cover a part of a proximal end side surface of the flange and a lower plate portion configured to cover a part of a distal end side surface of the flange.

9. The syringe barrel grip configured to be attached to the syringe barrel according to claim 1, wherein the first pair of grip straight portions that are spaced apart from one another are parallel to one another.

10. The syringe barrel grip configured to be attached to the syringe barrel according to claim 1, the second pair of grip straight portions that are spaced apart from one another are parallel to one another.

11. A barrel assembly comprising: a syringe barrel including a cylindrical body and a flange disposed at a proximal end of the cylindrical body, protruding outward, and including a pair of flange straight portions that are parallel to one another and disposed on the flange at positions opposite one another; and the syringe barrel grip according to claim 1 attached to the barrel.

12. A syringe comprising:

a barrel assembly comprised of a syringe barrel and a syringe barrel grip, the syringe barrel including a cylindrical body and a flange disposed at a proximal end of the cylindrical body, the flange protruding outward away from the cylindrical body and including a pair of flange straight portions that are parallel to one another and that face away from one another, the flat straight portions being spaced apart from each other by a first width;

a gasket slidably housed in the cylindrical body of the syringe barrel; and a plunger positionable in the cylindrical body of the syringe barrel for slidably moving the gasket in the cylindrical body of the syringe barrel;

the syringe barrel grip comprising:

a flange housing portion in which is positioned the flange of the syringe barrel;

the flange housing portion including: a side surface opening formed on a side surface of the syringe barrel grip through which the flange of the syringe barrel passes as the flange of the syringe is introduced into the flange housing portion; a flange rotation restricting portion in which the flange is positioned and that restricts relative rotation between the syringe barrel grip and the flange; and a flange insertion portion between the side surface opening and the flange rotation restricting portion, the flange insertion portion being configured to receive the flange of the syringe barrel that has passed through the flange insertion portion and before the flange of the syringe barrel is moved to the flange rotation restricting portion of the flange housing portion;

the flange insertion portion including a first pair of grip straight portions spaced apart from one another by a second width that is greater than the first width, and the flange rotation restricting portion including a second pair of grip straight portions spaced apart from one another by a third width that is greater than the first width, each of the second pair of grip straight portions being inclined with respect to a respective one of the first pair of grip straight portions;

the flange being positioned in the flange rotation restricting portion of the flange housing portion such that front sides of the pair of flange straight portions are located between the second pair of grip straight portions, and rear sides of the pair of flange straight portions are located between the first pair of grip straight portions; and the flange being positioned in the flange rotation restricting portion of the flange housing portion such that a lower inner peripheral surface of the grip is not in contact with the barrel so that a gap exists between the lower inner peripheral surface of the grip and the barrel, the gap allowing a sterilization gas to flow between the lower inner peripheral surface of the grip and the barrel.

13. The syringe according to claim 12, wherein a distal end side portion of the plunger is configured to be positioned in the cylindrical barrel, and the plunger includes a stopper portion that is disposed in the distal end side portion in the cylindrical barrel, the stopper being configured to abut on the grip, and restrict detachment of the plunger from the barrel.

14. The syringe according to claim 13, wherein the plunger includes a gasket pressing portion having a distal end that abuts on a proximal end portion of the gasket when the plunger is positioned in the cylindrical body of the syringe barrel.

15. The syringe according to claim 12, further comprising a drug stored in the cylindrical barrel between the gasket and a distal-most end of the cylindrical barrel.

16. The syringe according to claim 12, wherein one of the first pair of grip straight portions along one side of the flange insertion portion and one of the second pair of grip straight portions along the one side of the flange insertion portion are separated from each other by a protrusion.

17. The syringe according to claim 16, wherein the other one of the first pair of grip straight portions along an other side of the flange insertion portion and the other one of the second pair of grip straight portions along the other side of the flange insertion portion are separated from each other by a stepped portion.

18. The syringe according to claim 16, wherein the other one of the first pair of grip straight portions along an other side of the flange insertion portion and the other one of the second pair of grip straight portions along the other side of the flange insertion portion are directly connected to one another.

19. The syringe according to claim 12, the first pair of grip straight portions that are spaced apart from one another are parallel to one another, and the second pair of grip straight portions that are spaced apart from one another are parallel to one another.

20. A method comprising:

introducing a flange at one end of a cylindrical syringe barrel into a side surface opening located on a side surface of a flange housing portion of a syringe barrel grip, the flange protruding outwardly away from the cylindrical body and including a pair of flange straight portions parallel to one another and spaced apart by a first distance, the flange housing portion also including a flange insertion portion extending in an internal direction of the syringe barrel grip from the side surface opening, and a flange rotation restricting portion that communicates with the flange insertion portion, the flange insertion portion includes a first pair of grip straight portions spaced apart by a distance that is greater than the first distance, the flange rotation restricting portion including a second pair of grip straight portions spaced apart by a distance that is greater than the first distance;

moving the flange which has been introduced into the side surface opening into the flange insertion portion of the flange housing portion such that the pair of flange straight portions are located between the first pair of grip straight portions of the flange insertion portion, each of the second pair of grip straight portions being inclined with respect to a respective one of the first pair of grip straight portions;

relatively rotating the cylindrical syringe barrel and the syringe barrel grip while the flange of the cylindrical syringe barrel is in the flange insertion portion to move the flange from the flange insertion portion of the flange housing portion of the syringe barrel grip to the flange rotation restricting portion of the flange housing portion of the syringe barrel grip, the flange of the cylindrical syringe barrel located in the flange rotation restricting portion of the flange housing portion of the syringe barrel grip being positioned so that front sides of the pair of flange straight portions are located between the second pair of grip straight portions, and rear sides of the pair of flange straight portions are located between the first pair of grip straight portions; and the flange of the cylindrical syringe barrel located in the flange rotation restricting portion of the flange housing portion of the syringe barrel grip being configured so that a gap for allowing a sterilization gas to flow between a lower inner peripheral surface of the grip and the cylindrical syringe barrel.

* * * * *